United States Patent [19]

Chen et al.

[11] Patent Number: 4,480,089

[45] Date of Patent: Oct. 30, 1984

[54] MODIFIED CELLULOSE PRODUCTS BY BLEACHING

[75] Inventors: Li F. Chen; Parakkat Seethanathan, both of West Lafayette, Ind.

[73] Assignee: Purdue Research Foundation, West Lafayette, Ind.

[21] Appl. No.: 504,062

[22] Filed: Jun. 14, 1983

[51] Int. Cl.$^3$ .................. C08B 1/00; A61K 9/20; D21C 9/10

[52] U.S. Cl. .................. 536/56; 8/108 A; 8/108 R; 162/66; 162/87; 424/362

[58] Field of Search ............ 8/108 R, 108 A; 162/66, 162/87; 536/56; 424/362

[56] References Cited

U.S. PATENT DOCUMENTS

| | | | |
|---|---|---|---|
| 2,046,551 | 7/1936 | Davies | 162/88 |
| 2,100,496 | 11/1937 | Taylor et al. | 162/88 |
| 2,663,907 | 12/1953 | Downing et al. | 536/56 |
| 2,978,446 | 4/1961 | Battista et al. | 536/56 |
| 3,020,197 | 2/1962 | Schuber | 8/108 R |
| 3,976,538 | 8/1976 | Gullichsen et al. | 8/108 R |
| 3,992,250 | 11/1976 | Chaudhuri et al. | 8/108 R |
| 4,081,317 | 3/1978 | Gall et al. | 8/108 A |
| 4,236,891 | 12/1980 | Scardera et al. | 8/108 R |
| 4,269,859 | 5/1981 | Morse | 536/56 |

FOREIGN PATENT DOCUMENTS 1374770  8/1964  France .................. 8/108 R

*Primary Examiner*—Ronald W. Griffin
*Attorney, Agent, or Firm*—Cushman, Darby & Cushman

[57] ABSTRACT

Modified cellulose products for use as carrier vehicles in forming cosmetics, pharmaceutical preparations, insecticides, etc. are prepared by treating a minimum weight ratio of about 10:1 of fibrous cellulosic material with an alkali metal or alkaline earth metal hypohalite (e.g. sodium hypochlorite) at a temperature of from about 15° to 60° C. for a period of time sufficient to render the material non-fibrous (i.e. pH drop to about 6 or less), filtering and washing obtain the desired product.

24 Claims, No Drawings

MODIFIED CELLULOSE PRODUCTS BY BLEACHING

BACKGROUND OF THE INVENTION

The cellulosic polymers are widely used in the preparation of food, plastics, textiles, pharmaceuticals, and others. Cellulose is the most readily available raw material in the world owing to the fact that it is the chief constituent of nearly all forms of plant life. Cellulose constitutes over 98% of cotton fiber, as much as 50% of most wood fiber and about 35% of cereal straws. Cellulose is a linear homopolymer of anhydroglucose units linked together by $\beta$-D-1,4 glycosidic bonds. X-ray diffraction and other evidence indicate that callulose microfibers are partially crystalline and partially amorphous. On the average, the structure of natural cellulose is considered to compose about 15% of amorphous and 85% of crystalline. The degree of polymerization of native cellulose generally ranges from 1,000 to 10,000. Studies of chemical derivatives confirm the existence of one primary hydroxyl group and two secondary hydroxyl groups for each anhydroglucose unit. These hydroxyl groups provide sites for the important chemical reactions of cellulose leading to the preparation of useful products. By chemical modification, a number of functional properties can be introduced in comparatively inexpensive modified cellulose.

The bleaching of cellulose materials with hypochlorites has been known for many years. Primarily bleaching has been employed to remove undesirable color bodies from the cellulose material by utilizing relatively a high pH (ie. about 9 or above) which is maintained throughout the bleach cycle, resulting in a raw cellulose fiber material (i.e. dissolving grade cellulose-DGC) suitable for the production of rayon, paper, etc. The reaction of cellulose with hypochlorites at an uncontrolled pH below 9 has been studied, but no apparent use of the resulting product is known. We have found that the treatment of cellulose materials with appropriate amounts of hypochlorites at a suitable low pH results in a chemically modified cellulose material which is suitable as a carrier vehicle for a wide variety of active, cosmetic, pharmaceutical and the like preparations.

Accordingly, it is the primary object of the present invention to provide a modified cellulose product suitable for use as a carrier vehicle for a wide variety of materials.

A further object of the present invention is to provide a bodying agent composed of a modified cellulose.

Still another object of the present invention is to provide a method for modifying celluose to produce useful carrier vehicles and bodying agents.

These and other objects of the present invention will be more apparent from the discussion which follows.

SUMMARY OF THE INVENTION

The present invention provides a method for making a modified cellulose product which may be employed as a carrier vehicle or bodying agent. According to the invention fibrous cellulose material is treated with an alkali metal or alkaline earth metal hypohalite at a temperature ranging from 15° to 60° C. in an aqueous medium for a period of time sufficient to render the material non-fibrous. It is important that the initial weight ratio of fibrous material to hypohalite be at least 10:1 and that the aqueous medium (e.g. water) be present in a sufficient quantity to uniformly wet the fibrous material. Subsequently, the treated material is filtered and washed to remove salts and thereby obtain a modified cellulose product.

Although celluose may be bleached by various means, such as hydrogen peroxide, peracetic acid, chlorine dioxide and the like, it is preferred for the purposes of the present invention to employ an alkali metal or alkaline earth metal hypohalite, especially sodium or calcium hypochlorite. It is also known that bleaching may be either drastic or mild. For the purpose of the present invention, drastic bleaching is effected by subjecting the cellulose to a concentrated hypochlorite bleach solution at room temperature for a period of time which may vary from 30 minutes to 24 hours depending on the nature of the cellulosic starting material. This drastic bleaching also removes other impurities from the cellulose.

It is also noted that the drastically bleached cellulose forms a thixotropic gel when agitating with water. The drastically bleached cellulose particle size varies from less than a micron to more than a hundred microns in size. The particle size distribution depends on the starting material such as wood pulp or cotton linter. Thus, modified cotton linter forms a uniform, continuous and transparent film on a glass plate, whereas wood pulp forms a rather opaque film due to the polydispersity of the particle size.

Critical to the obtaining of desired cellulose material is the concentration of hypochlorite and pH conditions under which processing is carried out. In contrast to the known methods of bleaching cellulose materials wherein alkali is added at intervals or continually throughout the bleaching process so as to maintain a relatively high pH, the present mode of treatment simply involves an initial charge of hypohalite without the need for further addition. Thus, whereas known bleaching methods maintain the pH at e.g. 9 or above, in the present invention the pH is permitted to drop (e.g. from about 12 to as low as about 2) during treatment.

Suitable cellulose starting materials include any cellulose material, but preferably dissolving grade cellulose, such as cotton linter, purified wood pulp, alpha cellulose and like materials. Non-dissolving grade cellulose materials (e.g. bagasse, sawdust, corn or stover, etc.) may also be utilized depending on the final product usage.

By way of explanation, and not wishing to be limited thereby, the modified cellulose of the present invention is a cellulose material wherein the hydroxyl groups in the 2, 3 and/or 6 position of the anhydroglucoside segments of the amorphous portion have been converted to carbonyl groups with concurrent splitting of some of the beta 1-4 linkages.

It is desirable that this modified cellulose not be soluble in water or organic solvents. Modified cellulose may function as a vehicle or bodying agent similar to many hydrocolloids with proper formulation. Desirably, the modified cellulose can form a gel or cream which when formulated with a suitable active ingredient can be used for many topical applications such as cosmetics, pharmaceuticals, and personal care products. The modified cellulose of the present invention forms a nongreasy, non-tacky, transparent, uniform, clear, continuous film when applied as a lotion, gel or cream on the skin. Many active ingredients like N,N,diethyl-m-toluamide (insect repellent) and Amerscreen-P (sunscreen) can be readily incorporated in this cellulose gel system. The advantage is that cellulose is the basic material of film formation. It will not easily wash off by swetting or perspiration.

U.S. Pat. No. 2,978,446 describes a method to produce microcrystalline cellulose wherein the amorphous regions of cellulose are either degraded or dissolved away leaving the crystalline regions as fine crystals. In this process, hydrochloric acid is used to hydrolyze the amorphous portion of cellulose. U.K. patent application No. 2,066,145A describes a method to produce microfibrilated cellulose. According to this process, a liquid suspension of fibrous cellulose is passed through an orifice wherein the suspension is subjected to a pressure drop of 3000 psi and a high velocity shearing action followed by a high velocity decelerating impact. The suspension is repeatedly passed through the orifice until the cellulose suspension becomes a substantially stable suspension.

The present process to obtain modified cellulose does not hydrolyze the amorphous portion of the cellulose, but rather introduces functional carbonyl groups to the amorphous region to modify the cellulose. During this reaction, the bonds between cellulose crystals are broken and the cellulose loses its fibrous structure. Thus, the modified cellulose produced by the present method has different properties from the products produced by high pH methods.

DETAILED DESCRIPTION OF THE INVENTION

According to the invention, there is provided a process for the preparation of modified cellulose by bleaching fibrous cellulose with an alkaline solution of a hypohalite. After the reaction is completed, the resulting cellulose suspension is washed to remove salts, and then, if desired, homogenized to form a lotion, gel or cream. This modified cellulose is insoluble in water as well as organic solvents. If a suspension of the modified cellulose in water is spread in a thin layer on a glass plate and allowed to dry, a strongly adherent continuous film results.

It is known that hypochlorite bleaching causes the production of a number of carboxyl and carbonyl groups on the amorphous portion of the polymer molecule. Simultaneously there is a splitting of the glycosidic bonds which results in an overall decrease in molecular size. By careful control of temperature, pH and concentration of hypochlorite according to the present invention, the cellulose can be modified to obtain useful properties.

The temperature at which the fibrous cellulose is subjected to bleaching is not critical, but should be within the range of about 15° to 60° C., and preferably within the range of about 40° to about 60° C.

Addition of hypohalite to the fibrous material at a minimum concentration of at least 0.1 (based on the weight of the cellulose) is essential. Greater amounts of hypohalite may be employed, but generally a ratio of from about 0.1 to 1 by weight hypohalite to cellulose is sufficient. While the initial pH of the reaction mixture will be rather high (e.g. 12 or greater), as the treatment proceeds to render the cellulose non-fibrous, the pH window will drop to generally between 2 and 9, and generally below 6.

The hypohalite may be generated in situ in the process by addition of elemental chlorine or bromine to the aqueous medium containing caustic lime or soda.

While sodium and calcium hypochlorite are employed as preferred hypohalites herein, other alkali metal or alkaline earth metal hyppohalites may be used including: sodium hypobromite, calcium hypobromite, potassium hypochlorite, magnesium hypochlorite and like materials.

The time period for processing of the fibrous cellulose material is not critical, but should be sufficient to render the material non-fibrous. Generally, from one-half to 24 hours is sufficient.

If desired, the filtered and washed product may be dried or alternatively resuspended in water and/or a water-miscible solvent for use as a carrier vehicle for active ingredient materials. Suitable water-miscible solvents include $C_1$ to $C_6$ alcohols, glycerol and its water soluble esters, polyglycerol esters, $C_2$ to $C_4$ ketones, polyglycols and glycols.

If desired, the product may be compressed, optionally with other ingredients, to a shape retentive form without the need of an added binder. Thus, the dried modified cellulose may be blended with a foodstuff or active pharmaceutical material and compressed to form a tablet, block, stick or briquette. Likewise, the dried modified cellulose can be blended with active fertilizer components, insecticides, rodenticides, and herbicides to provide useful products which may have desirable slow-release properties. Generally, at least about 70 percent by weight of the solid product should comprise the cellulose material, although lesser amounts can be employed where the active ingredient contributes to the binding of the product.

Resuspension and homogenization of the modified cellulose with water and/or a water-miscible solvent provides compositions of varying physical properties depending upon the particular solvent and modified cellulose concentration. Generally speaking, resuspension of from about 0.5 to 5 percent modified cellulose in water or a water-miscible solvent produces a creamy white suspension stable for extended periods of time. Concentrations of from about 5 to about 10 percent generally take the form of a gell, while higher concentrations (e.g. about 10 to 50 percent) will produce a cream.

The following examples are offered to more fully illustrate the invention, but are not to be construed as limiting the scope thereof.

EXAMPLE 1

A 1-liter stainless steel vessel equipped with a stirrer was charged with 20 grams of wood pulp, 20 grams of calcium hypochlorite, and 400 mls. of water. The resulting mixture was stirred at room temperature (i.e. about 20° C.) under a hood overnight. The initial pH of the mixture was greater than 12 and dropped during reaction to below 4 at which time the reaction was complete and the non-fibrous suspension was filtered and washed with water to remove salts. The salt free cellulose product was resuspended (10% by weight cellulose) in water and subjected to a high shear homogenization in a homogenizer which resulted in the formation of a thixotropic gel. The product, if desired, can be dried before or after homogenization.

EXAMPLE 2

To a stainless steel vessel equipped with a stirrer was charged 20 grams of cotton linter and 400 mls. of a 5% sodium hypochlorite solution. The vessel was left overnight as in Example 1 until the pH dropped to below 4.

The reaction mixture was filtered, washed and resuspended in water as in Example 1. Upon subjecting the resuspended product to high shear homogenization a thixotropic gel was formed.

EXAMPLE 3

450 grams of wood pulp were placed in a stainless steel vessel equipped with a stirrer and gas inlet tube positioned near the bottom of the vessel. The wood pulp was thoroughly soaked in 8 liters of a 2% caustic soda solution. Thereafter, chlorine gas was bubbled into the mixture until the pH dropped to 4 and the cellulose became nonfibrous. The cellulose suspension was filtered, washed and resuspended in water (10% by weight) and homogenized to form a thixotropic gel.

EXAMPLE 4

The procedure of Example 1 was repeated using cotton linter in place of wood pulp to produce a cream comprising 30% of the cellulose product in water. To 100 grams of the cream was added 2.5 grams of Pluronic F108 (a non-ionic surfactant) and 30 grams of rose oil with stirring. This resulted in a fragrant cream product suitable for topical application or alternatively as an air freshener.

EXAMPLE 5

The procedure of Example 4 was repeated using 30 grams of lemon oil instead of rose oil. The resulting cream provided a fragrant product suitable for use as an air freshener.

EXAMPLE 6

The procedure 1 was repeated using cotton linter in place of wood pulp to produce a thick lotion having from 10 to 15% of the cellulose material in water. To 100 grams of the lotion was added 5 grams of Pluronic F108. 5 grams of Amerscreen-P (a commercially available active sunscreen) was dissolved in 10 ml. of ethanol, mixed and added with stirring to the cellulose/Pluronic lotion mixture. The resulting lotion when spread on human skin formed a uniform, non-tacky film which on drying would not easily wash off with water.

EXAMPLE 7

The procedure of Example 1 was repeated using cotton linter in lieu of wood pulp to form a 20% cellulose in water cream. To 100 grams of the cream was added 2.5 grams of Pluronic F108, and 15% of N,N,diethyl-m-toluamide (DEET), an active mosquito repellent. The resulting cream when topically applied to skin provides an effective degree of insect repellency.

EXAMPLE 8

Wood pulp was treated as in Example 1 to form a 30% cellulose/water cream to which was added 2.5% Pluronic F68 surfactant (non-ionic) and 33% DEET to form a very thick cream. The product exhibited the uniform, non-tacky film properties as noted in Example 7. The cream product exhibits effective repellency to mosquitoes, and house flies for a period of 5 to 5½ hours when topically applied to the skin.

EXAMPLE 9

Cotton linter was treated in the same manner described in Example 1 to provide 100 grams of a 20% cellulose/water cream to which was added 2.5% of Pluronic F108. Separately, 9 grams of menthol were dissolved in 18 grams of methyl salycilate, and the mixture was added to the cellulose cream with stirring, resulting in a liniment cream suitable for topical application.

EXAMPLE 10

100 grams dried bagasse from sugar cane, which has been treated to remove the hemicellulose portion, was treated in the same manner as Example 1 with 100 grams of calcium hypochlorite in 1 liter of water. The ligno-cellulose product was centrifuged and washed with water to remove salt and other coloring matter. The washing was repeated three times. The filtered residue was resuspended to form a 30% suspension in water and subjected to high shear homogenization in a blender for 45 minutes at maximum speed. The resulting yellow cream paste was resuspended in water to a 5% concentration and cast as a film on a petri dish. Upon drying, there was observed a non-tacky, continuous, yellow film.

EXAMPLE 11

The procedure of Example 10 is repeated to form a 20% cream of the ligno-cellulose/water cream to which is added 2% of flowered pyrethrin extract. The resulting product is suitable as an indoor insecticide.

The invention having been thus described, it will be appreciated that various departures can be made therefrom within the scope of the following claims.

We claim:

1. A method of making a modified cellulose product suitable for use as a carrier vehicle or bodying agent comprising the steps of treating a fibrous cellulose material with an alkali metal or alkaline earth metal hypohalite at a temperature ranging from about 15° to about 60° C. in an aqueous medium for a period of time sufficient to render the material non-fibrous, the weight ratio of fibrous cellulose material to hypohalite being from about 10:1 to 1:1 and the aqueous medium being present in a sufficient quantity to achieve uniform wetting of the fibrous material, filtering and washing the reaction material to remove salts and obtain a modified cellulose product.

2. A method according to claim 1 wherein said hypohalite is generated in-situ by the addition of elemental chlorine to the aqueous medium which contains caustic lime or soda.

3. A method according to claim 1 wherein said hypohalite is selected from the group consisting of sodium hypochlorite and calcium hypochlorite.

4. A method according to claim 3 wherein the said period of time is sufficient that the pH of the medium has dropped to about 6 or less.

5. A method according to claim 3 wherein the said period of time is sufficient that the pH of the medium has dropped to about 4 or less.

6. A method according to claim 1 wherein the product is resuspended in a liquid medium selected from the group consisting of water, a water miscible solvent and mixtures thereof, and subjected to high shear homogenization to produce a suspension, gel or cream.

7. A method according to claim 6 wherein from about 0.5 to about 50% by weight of said product is resuspended in the liquid medium.

8. A method according to claim 7 wherein from about 5 to about 10% by weight of said product is resuspended in the liquid medium and subjected to high shear homogenization to produce a thixotropic gel.

9. A method according to claim 6 wherein the suspension, gel or cream is dried.

10. A method according to claim 1 wherein the product is dried.

11. A method according to claim 1 wherein said fibrous cellulose material is purified wood pulp, cotton linter or cotton fibers.

12. A method according to claim 1 wherein said fibrous cellulose material is bagasse, corn stover or sawdust.

13. A method according to claim 1 wherein said temperature is room temperature.

14. A method according to claim 1 wherein said temperature is from about 30° to about 50° C.

15. A method according to claim 1 wherein the product is dried and combined with an active ingredient and compressed to a shape retentive form.

16. A method according to claim 15 wherein said form is a tablet, block, stick or briquette.

17. A method according to claim 6 wherein said product is resuspended together with an active ingredient in the liquid medium to form said suspension, gel or cream.

18. A method according to claim 17 wherein the suspension, gel or cream is dried to remove the liquid medium.

19. A method according to claim 17 wherein the active ingredient is an edible foodstuff.

20. A method according to claim 17 wherein the active ingredient is a pharmaceutical compound or composition.

21. A method according to claim 17 wherein the active ingredient is an insecticide, herbicide, rodenticide or fungicide.

22. A method according to claim 17 wherein the active ingredient is a fertilizer.

23. A method according to claim 17 wherein the active ingredient is a cosmetic composition.

24. A method according to claim 17 wherein the active ingredient is a pigment containing composition.

* * * * *